United States Patent
Vignon et al.

(10) Patent No.: US 10,702,248 B2
(45) Date of Patent: Jul. 7, 2020

(54) ULTRASOUND ACQUISITION FEEDBACK GUIDANCE TO A TARGET VIEW

(71) Applicant: KONINKLIJKE PHILIPS N.V., Eindhoven (NL)

(72) Inventors: Francois Guy Gerard Marie Vignon, Croton On Hudson, NY (US); Vijay Parthasarathy, Mount Kisco, NY (US); Ajay Anand, Fishkill, NY (US); Ameet Kumar Jain, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 378 days.

(21) Appl. No.: 14/901,104

(22) PCT Filed: Jun. 23, 2014

(86) PCT No.: PCT/IB2014/062523
§ 371 (c)(1),
(2) Date: Dec. 28, 2015

(87) PCT Pub. No.: WO2014/207642
PCT Pub. Date: Dec. 31, 2014

(65) Prior Publication Data
US 2016/0143627 A1    May 26, 2016

Related U.S. Application Data

(60) Provisional application No. 61/840,727, filed on Jun. 28, 2013.

(51) Int. Cl.
*A61B 8/08*    (2006.01)
*A61B 8/00*    (2006.01)
(Continued)

(52) U.S. Cl.
CPC .............. *A61B 8/5269* (2013.01); *A61B 8/08* (2013.01); *A61B 8/461* (2013.01); *A61B 8/466* (2013.01);
(Continued)

(58) Field of Classification Search
CPC ....... A61B 8/08; A61B 8/0891; A61B 8/4416; A61B 8/461; A61B 8/463; A61B 8/466;
(Continued)

(56) References Cited

U.S. PATENT DOCUMENTS 5,906,578 A * 5/1999 Rajan ................. A61B 1/00009
                                                                  600/424
7,074,185 B2    7/2006 Takeuchi
(Continued)

FOREIGN PATENT DOCUMENTS

JP    2009089736 A    4/2009

OTHER PUBLICATIONS

Snare, S.R. et al "Real-Time Scan Assistant for Echocardiography", IEEE Transactions in Ultrasonics, Ferroelectrics, and Frequency Control, 2012.
(Continued)

*Primary Examiner* — Amelie R Davis (57) ABSTRACT

Systems, devices, and associated methods including: emitting ultrasound to the subject and receiving, in response, a current ultrasound view; matching the received image to a pre-existing image, such as a three-dimensional reference image; and, for user assistance, generating, based on the matching, feedback for the guidance. The reference image may be a statistical atlas or it may be derived from patient-specific CT or MR scans. The pre-existing image may instead be a database image corresponding to a state in a state space. The feedback can be an image derived from the reference image; a graphic indication of a plane of the target
(Continued)

view; the received view fused to an image derived from the reference image; or the received view and an image derived from the reference image, the derived image appearing concurrently and enhanced to spatially indicated where the received view registers to the reference image.

20 Claims, 7 Drawing Sheets (51) Int. Cl.
  *G06T 7/73* (2017.01)
  *G06F 16/583* (2019.01)
(52) U.S. Cl.
  CPC .............. *A61B 8/483* (2013.01); *A61B 8/488* (2013.01); *A61B 8/5292* (2013.01); *A61B 8/54* (2013.01); *G06F 16/583* (2019.01); *G06T 7/74* (2017.01); *A61B 8/0891* (2013.01); *A61B 8/4416* (2013.01); *A61B 8/463* (2013.01); *A61B 8/5207* (2013.01); *A61B 8/5215* (2013.01); *G06T 2207/10132* (2013.01); *G06T 2207/30004* (2013.01); *G06T 2207/30101* (2013.01); *G06T 2207/30244* (2013.01)
(58) Field of Classification Search
  CPC ....... A61B 8/483; A61B 8/488; A61B 8/5207; A61B 8/5215; A61B 8/5269; A61B 8/5292; A61B 8/54; G06T 2207/10132; G06T 2207/30004; G06T 2207/30101; G06T 2207/30244; G06T 7/74; G06F 16/583
  See application file for complete search history.

(56) References Cited

U.S. PATENT DOCUMENTS

| 7,221,972 | B2 | 5/2007 | Jackson |
| 8,352,494 | B1* | 1/2013 | Badoiu ............. G06F 17/30256 707/772 |
| 2005/0187472 | A1 | 8/2005 | Lysyansky |
| 2007/0081706 | A1* | 4/2007 | Zhou .................... G06F 19/321 382/128 |
| 2007/0173721 | A1 | 7/2007 | Lysyansky |
| 2010/0010348 | A1 | 1/2010 | Halmann |
| 2010/0331700 | A1 | 12/2010 | Baba et al. |
| 2012/0065510 | A1 | 3/2012 | Snare |

OTHER PUBLICATIONS

Engelhardt, Martin et al "A Training Station to Facilitate Transcranial Ultrasound Imaging", 2007 IEEE Untrasonics Symposium.

* cited by examiner

ULTRASOUND ACQUISITION FEEDBACK GUIDANCE TO A TARGET VIEW

CROSS-REFERENCE TO PRIOR APPLICATIONS

This application is the U.S. National Phase application under 35 U.S.C. § 371 of International Application No. PCT/IB2014/062523, filed on Jun. 23, 2014, which claims the benefit of U.S. Provisional Patent Application No. 61/840,727, filed on Jun. 28, 2013. These applications are hereby incorporated by reference herein.

FIELD OF THE INVENTION

The present invention relates to ultrasound image matching for user guidance and, more particularly, to such matching to a pre-existing image to achieve a target view.

BACKGROUND OF THE INVENTION

Successful ultrasound scanning relies strongly on the training and experience of the user. To avoid artifacts, the user has to place the probe in the right position, i.e., to find a good acoustic window, for imaging. Conventionally, this is done solely based on real-time ultrasound images displayed onscreen. Although experienced users are usually capable of recognizing image degradation, and of improving image quality accordingly by moving the probe to a better position, less experienced users might acquire compromised images because of inferior hand-eye coordination and less awareness of artifacts. Acquisition of a set of standard views of a body organ of interest is a challenging task for healthcare workers having little or no background in radiology.

"Real-Time Scan Assistant for Echocardiography", Snare, S. R. et al., IEEE Transactions in Ultrasonics, Ferroelectrics, and Frequency Control (2012) (hereinafter "the Snare publication") describes an image-processing approach applied to two-dimensional (2D) four-chamber cardiac images to output a metric of the quality of the obtained view.

SUMMARY OF THE INVENTION

What is proposed herein below is directed to addressing one or more of the above concerns.

The Snare publication rates the current view, but does not guide the user toward a target view.

A means by which the clinician can be automatically guided along a path to achieving a target view is needed.

In accordance with an aspect of the present invention, guidance in acquiring ultrasound imaging of a subject to achieve a target view includes emitting, via an imaging probe, ultrasound to the subject and, in response, receiving a current ultrasound view; matching the received image to a pre-existing image; and, via a user assistance module, generating, based on the matching, feedback for the guidance.

In a sub-aspect, the target view is a view of a body organ, or vessel, of the subject.

In another sub-aspect, the generating is performed dynamically or continually.

In a different sub-aspect, the probe has a current placement, and at least one of showing and instructing occurs on how to move the probe from its current placement so as to thereby realize the achieving of the target view.

In one sub-aspect, a match between the target view and the received view is detected.

As a further sub-aspect, an apparatus automatically, and without need for user intervention, performing either or both a) user notification responsive to the detecting of the match; and by acquiring image data, via the probe, responsive to the detecting of the match.

In one other sub-aspect, the target view is a standard anatomical view that, prior to a time of the guidance, has already been set by an authoritative medical entity.

In yet another sub-aspect, the feedback is presented.

As a further sub-aspect of this, the presenting is performed dynamically or continually.

In still another sub-aspect, the received view is registered to a three-dimensional reference image.

In a sub-aspect, the registering is performed dynamically or continually.

In one different sub-aspect, the reference image includes an atlas, an image acquired of the subject via medical imaging, or both the atlas and the image.

In a further sub-aspect, the atlas includes a statistical atlas.

As a further sub-aspect with regard to the view registering, an image derived from the reference image, and a graphic indication of a plane of the target view, are concurrently visualized.

In an additional or complementary sub-aspect of the view registering, there exists concurrent visualization of one or both of the following: the received view fused to an image derived from the reference image; and the received view and an image derived from the reference image, the derived image appearing concurrently and enhanced to spatially indicate where the received view registers to the reference image.

In another variation as a sub-aspect of the view registering, instruction is provided on how to move the probe for the achieving of the target view. A speaker for the instructing issues audible language instructions, instructions are issued on a display, or both the speaker and the display are provided for these purposes.

In a particular version of the above-mentioned aspect, a location of the received view in a state space is estimated.

In a particular sub-version of this, Doppler settings are, automatically by default, initialized according to those that were pre-set for the target view in building a database organized as the state space.

As a sub-version of this, a selection is made, based on the current ultrasound view, of a respective trajectory in the state space toward the target view.

As a further sub-version, the feedback is based on the selection.

In one added sub-version, the selection is made of an optimal trajectory in the state space toward the target view.

In a specific sub-version, a scanner configured for forming the state space does so by steps that include: acquiring, via the scanner and from multiple imaging subjects, images specialized for a specific body organ or vessel such that the organ or vessel, and/or surrounding tissue, are depicted in all of the plural images; and labeling the images with respective attributes.

In a further sub-version, forming the state space includes linking, to particular images such as those other than target, i.e., standard, images, respective instructions on how to navigate the probe from the particular image to another one of the images.

Details of the novel, real-time, interactive visual guidance technology are set forth further below, with the aid of the following drawings, which are not drawn to scale.

DETAILED DESCRIPTION OF EMBODIMENTS

Figure 1:
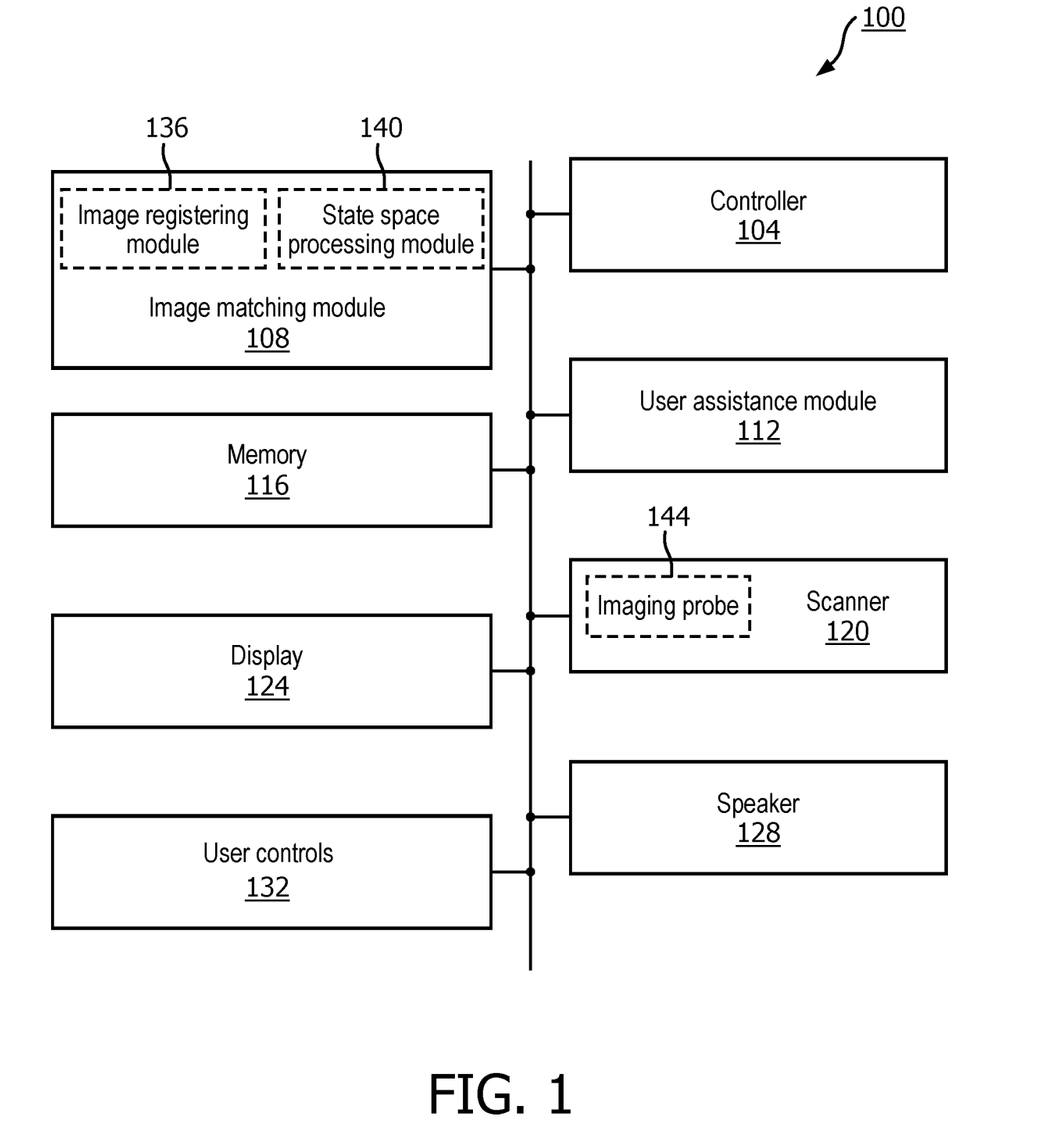
FIG. 1 is a schematic diagram of an ultrasound clinician interactive guidance apparatus in accordance with the present invention.

FIG. 1 depicts, by way of illustrative and non-limitative example, an ultrasound clinician interactive guidance apparatus 100. The apparatus 100 includes, among other component devices, a controller 104, an image matching module 108, a user assistance module 112, a memory 116, a scanner 120, a display 124, a speaker 128 and user controls 132. The image matching module 108 includes an image registering module 136 and/or a state space processing module 140. The scanner includes, among other component devices, an imaging probe 144.

Figure 2:
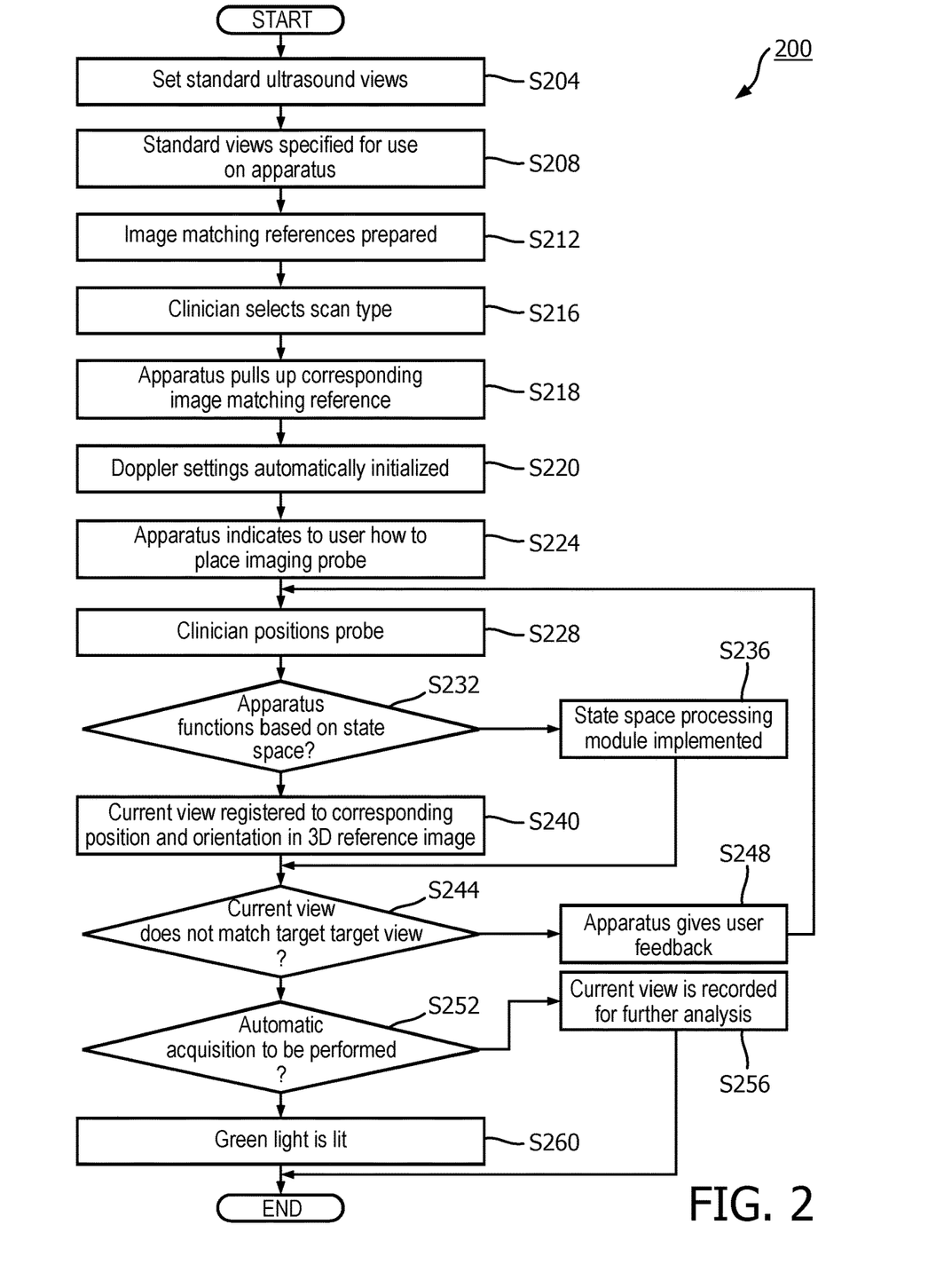
FIG. 2 is a flow chart of overall operation of one implementation of the apparatus of FIG. 1, in accordance with the present invention.

Operationally, an overall procedure 200 for ultrasound clinician interactive guidance is as follows, as shown in FIG. 2. As a preliminary step, an authoritative medical entity such as a physician, medical board, medical standards organization, or hospital sets standard ultrasound views for the body organ, or vessel, of interest (step S204). The set of standard views is specified for use on the apparatus 100 (step S208). One or more image matching references are prepared (step S212) which is explained in more detail below with reference to FIG. 3. The clinician selects a scan type, which may be for a particular body organ such as the heart, or vessel such a particular artery (step S216). The apparatus 100 pulls up the corresponding image matching reference (step S218). The apparatus 100 determines which target view from among the standard views is to be acquired next. The apparatus 100 also now loads Doppler settings that have been pre-selected for the target view, as discussed below in connection with FIGS. 4A and 4B. In short, Doppler settings are, automatically by default, initialized according to those that were pre-set for the target view in building a database organized as the state space (step S220). The apparatus 100 indicates to the user how, based on textbook guidelines for example, to place the imaging probe 144 on the superficial anatomy of the imaging subject, such as an animal or human patient (step S224). The user, i.e., clinician, positions the probe 144 (step S228). If the user guidance function apparatus 100 operates based on a state space (step S232), the state space processing module 140 is implemented and makes an estimate of the location, in the state space, of the current, or "live", view acquired via the probe 144 (step S236). If, on the other hand, the state space processing module 140 is not implemented (step S232) but the image registering module 136 is implemented, the current view is registered to a corresponding position, and orientation, in a three-dimensional (3D) reference image (step S240). If it is now determined that the current view does not match, or sufficiently represent, the target view (step S244), the apparatus 100 gives user feedback that instructs, or shows, how to proceed toward the goal of achieving the target view (step S248), and processing branches back to the user positioning step S228. Description in more detail of the feedback is provided further below in the discussion accompanying FIGS. 5 and 6. If, instead, a match has been attained (step S244) and automatic acquisition is to be performed (step S252), the current view is recorded for further analysis, e.g., by a physician (step S256). If, on the other hand, a match has been attained (step S244) and user-actuated acquisition is to be performed (step S252), a green light is lit on the probe 144 or elsewhere on the scanner, such as on a console that houses the user controls 132 (step S260).

Figure 3:
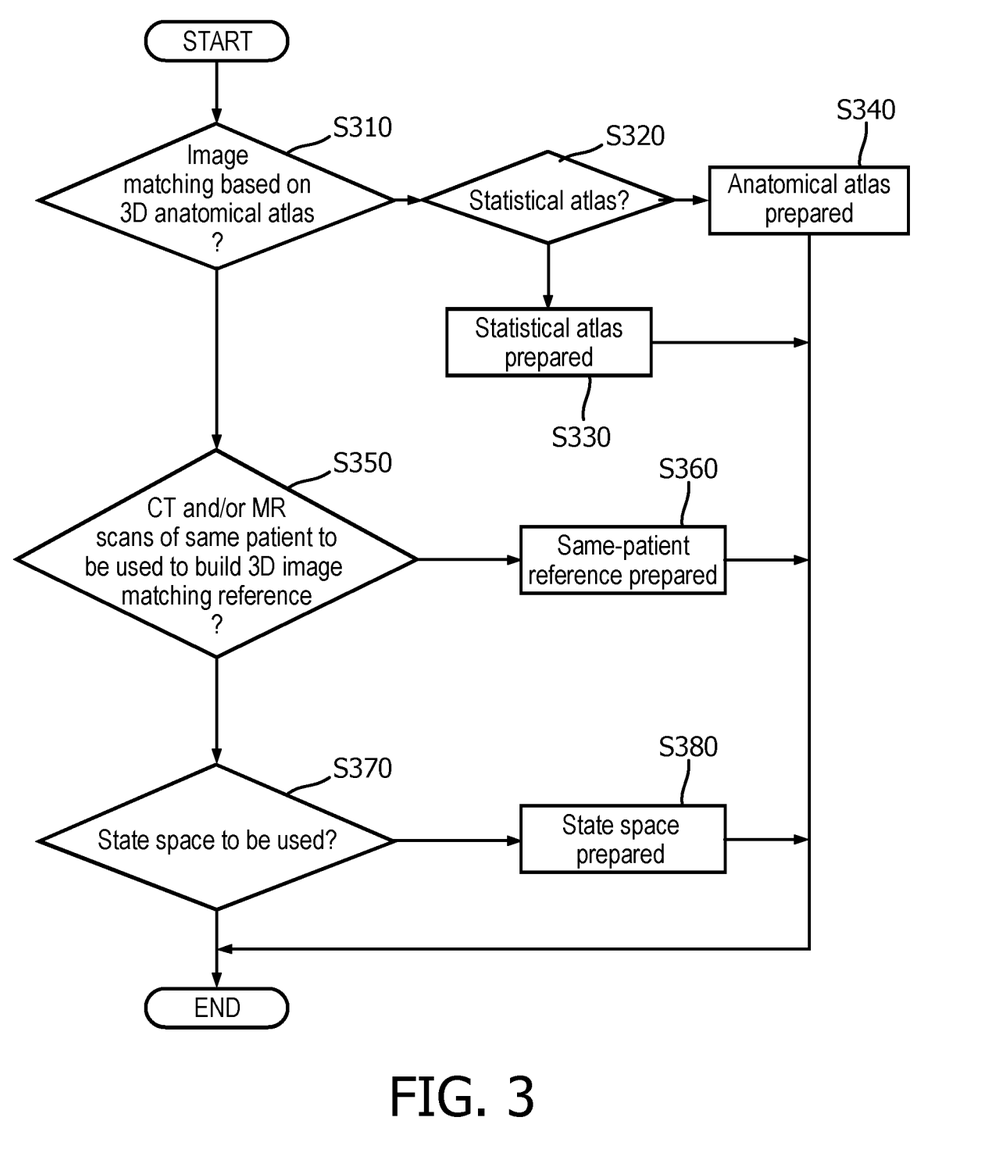
FIG. 3 is a flow chart of an example of image matching preparation, in accordance with the present invention.

The image matching reference preparation step (S212) is described in more detail in the flow chart of FIG. 3. With reference to FIG. 3, if image matching is to be based on a three-dimensional (3D) anatomical atlas as the image matching reference (step S310), and the atlas is to be a statistical atlas (step S320), a statistical atlas is prepared (step S330). The statistical atlas is built based on the computed tomography (CT) and/or magnetic resonance imaging (MR) scans of a wide variety of subjects to cover anatomical variation. It may be stored on a hard drive which is part of the memory 116. Per voxel, the atlas includes a distribution of image intensities reflective of individual members of the population. Neighboring information is also included for each voxel. Image matching to achieve registration is performed quicker due to the statistical nature of the statistical atlas. If, on the other hand, image matching is to be based on an anatomical atlas that is not a statistical atlas (steps S310, S320), the anatomical atlas is prepared as the 3D image matching reference, typically via CT and/or MR scans from a wide variety of subjects (step S340). If, instead of an atlas (step S310), CT and/or MR scans of the same patient are to be used to build the 3D image matching reference (step S350), the "same-patient" reference is prepared (step S360). If, on the other hand, the same-patient CT/MR scans are not available or are otherwise not to be used (step S350), and a state space is to be used (step S370), a state space is prepared (step S380). Preparation of the state space is described in more detail immediately below in connection with FIGS. 4A and 4B.

Figure 4A:
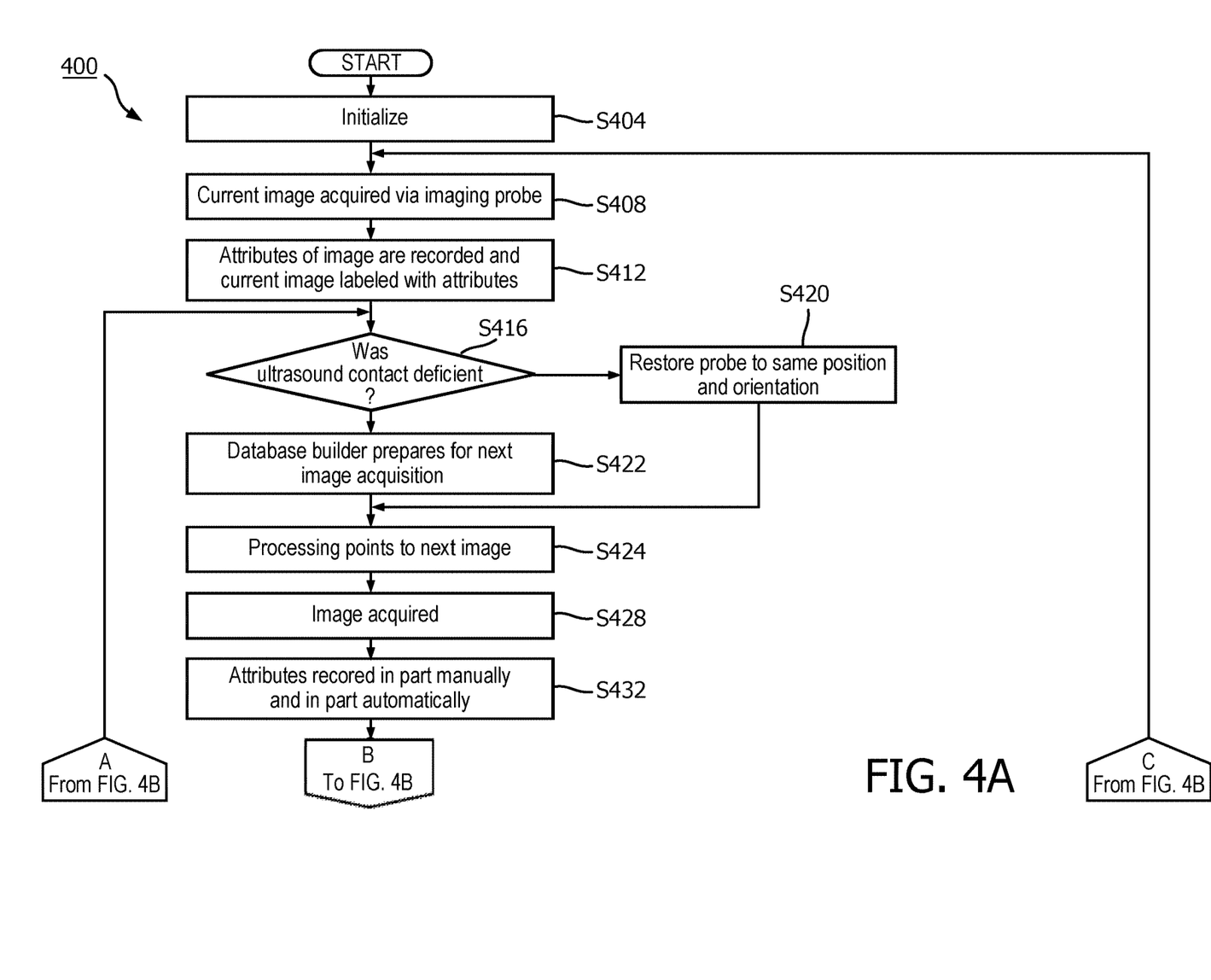
FIGS. 4A and 4B, collectively, are a flow chart of state space preparation, in accordance with the present invention.
Figure 4B:
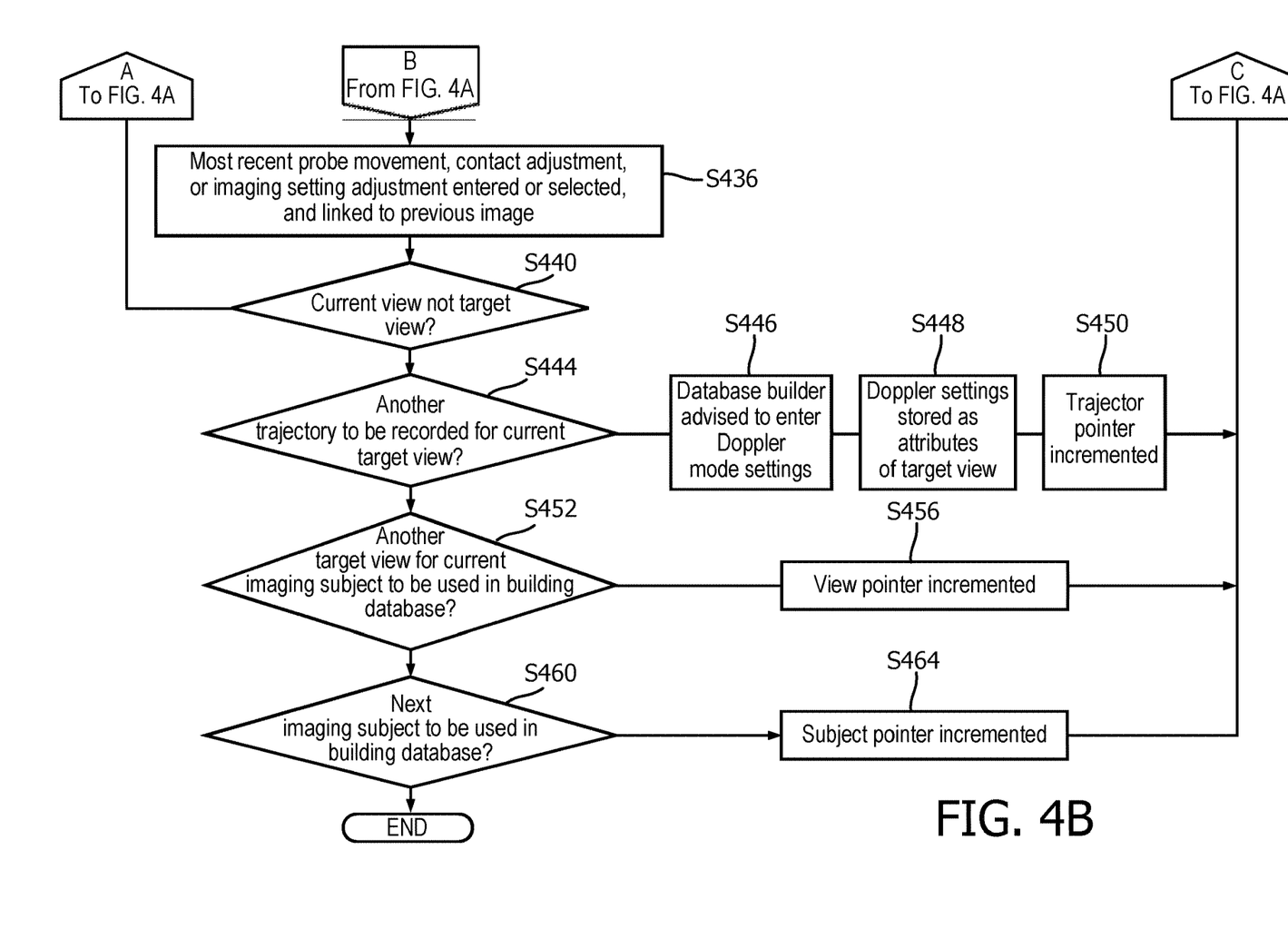

A state space preparation process 400 involves building a statistical database of a set of hundreds of scans of and around the organ, or vessel, of interest from multiple imaging subjects. The database is organized as a state space. Images to be incorporated into the state space are labeled with attributes such as viewed image anatomy, image quality, and corresponding probe position and orientation on the superficial anatomy. A subset of this set of images is the set of goal states, corresponding to the standard ultrasound views with good image quality. The images of the database can be described as points within a state space whose dimensions are the image attributes. Within the state space, it is possible to define a spatial relationship between ultrasound images, and in particular a trajectory between any ultrasound image and any of the goal images.

The images to be acquired for incorporation into the state space are specialized for a specific body organ, or vessel, such that the organ or vessel, and/or surrounding tissue, are depicted in each image. The process 400 is initialized to a first imaging subject, a first target view, a first trajectory and a first image (step S404). Thus, the respective pointers or counters are zeroed out. A current image is acquired via the imaging probe 144 (step S408). Attributes of the image are recorded and the current image is labeled with its attributes (step S412). The recording can be done in part automatically and in part via entry by the person building the database. The current image may be labeled according to: the viewed anatomy (e.g., carotid (left, right, common, internal, external, bulb, bifurcation, proximal, medial, distal, longitudinal, transverse, oblique, etc.) such as jugular vein, thyroid gland, vertebral bodies, vertebral artery, vertebral vein, subclavian artery, etc.; the position and orientation of the probe 144 with respect to the superficial anatomy to obtain these images (e.g., anterior, anterior, posterior, cranial, caudal, lateral, medial, neck, clavicle, mandible, Adam's apple, horizontal, vertical, oblique); optionally the current imaging mode and settings (e.g., for B-mode, power, focal depth, harmonics, spatial compounding; for color flow, gain, maximum velocity, color box orientation, sample volume size; and for spectral Doppler, maximum velocity and Doppler angle); and optionally the presence of artifacts and a measure of image quality (e.g., contact artifacts, good ultrasound contact and average image contrast). Labeling of the current imaging mode and settings is done automatically. Since navigation toward a target view ordinarily would proceed B-mode image to B-mode image, modes such as Doppler can ordinarily be, in effect, withdrawn from the navigation process. For example, these settings can be supplied by default automatically at the outset, as in step S220 above. The setting values were created according to control adjustments made by the database builder specifically for the target view during database build up. If, in the course of user navigation, the user inadvertently or for whatever reason, changes these settings, the resulting state space distance would automatically at some point of time, or points of time, during navigation, result in feedback offering user instruction for effectively restoring these settings. Alternatively, the target view Doppler settings need not be supplied by default upon initialization; instead, user feedback due to the resulting state space distance would, in the course of user navigation or at the outset, instruct the appropriate adjustments to the settings.

The current image acquired may have been acquired via ultrasound contact that is less than good. This would be done intentionally, so that matching to this image, once it is in the database, allows the deficient contact to be detected. If the contact is deficient (step S416), the person building the database applies or reapplies acoustic coupling medium, such as gel, restores the probe 144 to the same position and orientation with respect to the imaging subject for an improved image (step S420). Otherwise, if the contact was not deficient (step S416), the database builder, via probe movement or adjustment of imaging settings, prepares for a next image acquisition (step S422). The movement or adjustment is made so as to navigate toward the target image.

In either event, i.e., whether or not contact was sufficient, processing now points to that next image (step S424). The image is acquired (step S428). The attributes are recorded in part manually and in part automatically (step S432). The most recent probe movement, contact adjustment or imaging setting adjustment, ordinarily for B-mode, made in the corresponding above steps S420, S422 is entered or selected by the database builder, or automatically, and linked to the previous image, i.e., the image acquired just prior to step S428 (step S436). The entry could be, with respect to probe position, "left", "right", "up" or "down." Here, "up" would be mean generally in the head to toe direction. The entry could instead or in addition be, with respect orientation, i.e., tilting, "left", "right", "up", or "down." The entry could additionally or instead be, with respect in place rotation of the probe 144, "clockwise" or "counterclockwise." In each of these options, distance or magnitude need not be recorded, because the updating of the feedback loop in steps S228 to S248 occurs in real time. In particular, the database image having the location closest, according to Euclidean distance for example, to the estimate made in step S236 dynamically keeps the user on a trajectory toward the target view. Even if, during operation, a user wanders into another trajectory, that other trajectory will similarly navigate toward the target view. With regard to probe contact, the entry or selection by the database builder may be "reapply gel to probe and return to same position and orientation." For imaging setting changes, the automatic selection may be, for example, "increase imaging depth."

If the current view is not the target view (step S440), processing returns to step S416. Otherwise, if the current view is the target view as evidenced by actuation of the appropriate user control 132 by the database builder (step S440), and another trajectory is to be recorded for the current target view of the current imaging subject (step S444), the database builder is advised, via an onscreen message, to enter Doppler mode settings (step S446). Interactively, according to a series of screen prompts and responsive actuations by the database builder, the Doppler settings are stored as attributes of the target view (step S448). The trajectory pointer is incremented (step S450) and return is made to step S408. If, on the other hand, no such further trajectory is to be recorded (step S444), but another target view for the current imaging subject is to be used in building up the database (step S452), the view pointer is incremented (step S456) and return is likewise made to step S408. If, however, no target view for the current imaging subject remains in terms of building up the database (step S452), but a next imaging subject is to be used in building the database (step S460), the subject pointer is incremented (step S464) and return is likewise made to step S408.

Figure 5:
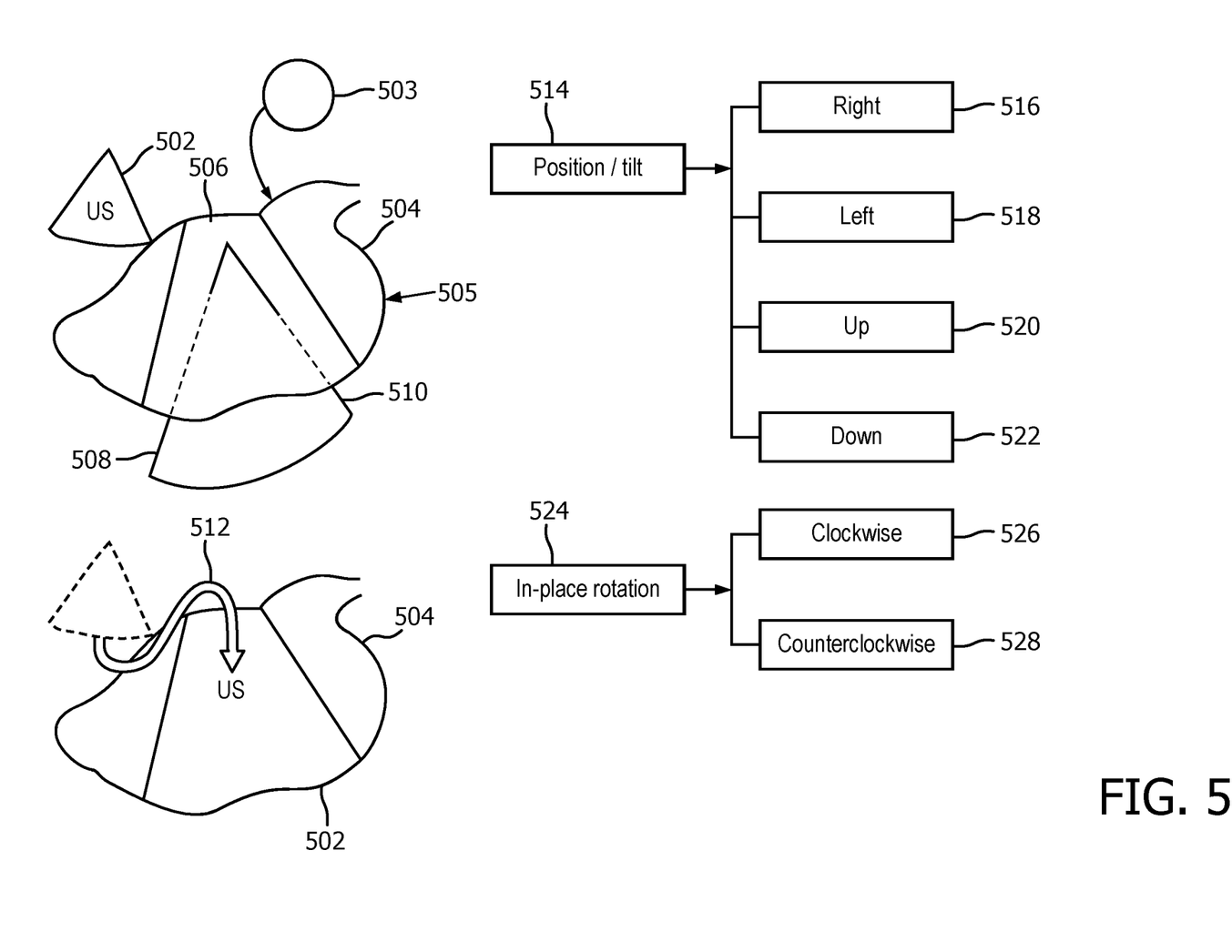
FIG. 5 is a conceptual and screen display diagram of examples of user feedback, in accordance with the present invention.

FIG. 5 provides examples of the user feedback of step S248, which can take the form of onscreen illustrations or messages, or audible language.

An ultrasound image representative of a current view 502 such as a B-mode image can be displayed alongside a cross-sectional image 504 derived from a 3D reference image 503 stored on a hard drive, i.e., from an atlas or from a 3D image constructed from patient-specific CT and/or MR scans. The cross-sectional image 504, here of a body organ 505, i.e., the heart, has been sectioned and enhanced to spatially indicate where the received (or "live") view registers to the reference image. Thus an enhanced region 506, that is colored for example, corresponds spatially with where the current image would cut into the atlas. To show the clinician how to proceed in navigating toward a current target view, a graphic indication 508 of the plane of the current target view 510 can be added to the onscreen presentation. Also, instead of showing the current view 502 as a separate image, the ultrasound image can be fused 512 to the cross-sectional image 504 such as by a pixel for pixel replacement. Here too, the graphic indication 508 can be added.

Alternatively or in addition, screen messages or audible language instructions can guide the clinician. Thus, for the position/tilt 514 of the probe 144, four possible indications 516-522 are "right", "left", "up" and "down", just as in the state space based embodiment. Likewise, as in the state space based embodiment, in-place rotation 524 can be "clockwise" 526 or "counterclockwise" 528.

The registration in step S240 involves image-based pattern matching of the current view 502 to the 3D reference image and a coordinate transformation on the current view to bring it into registration with the 3D image in accordance with the matching. The feedback instructions, based on the transformation, can be representative of a single kind, or more than one kind, of suggested probe movement 514, 524.

For the state space based embodiment, the estimate in step S236 is made as a result of pattern recognition from comparisons between the current view 502 and the database images acquired in the acquisition steps S408, S428. The one or more types of feedback instructions (i.e., probe movement, probe contact and imaging settings) linked to the current database image are presented.

Figure 6:
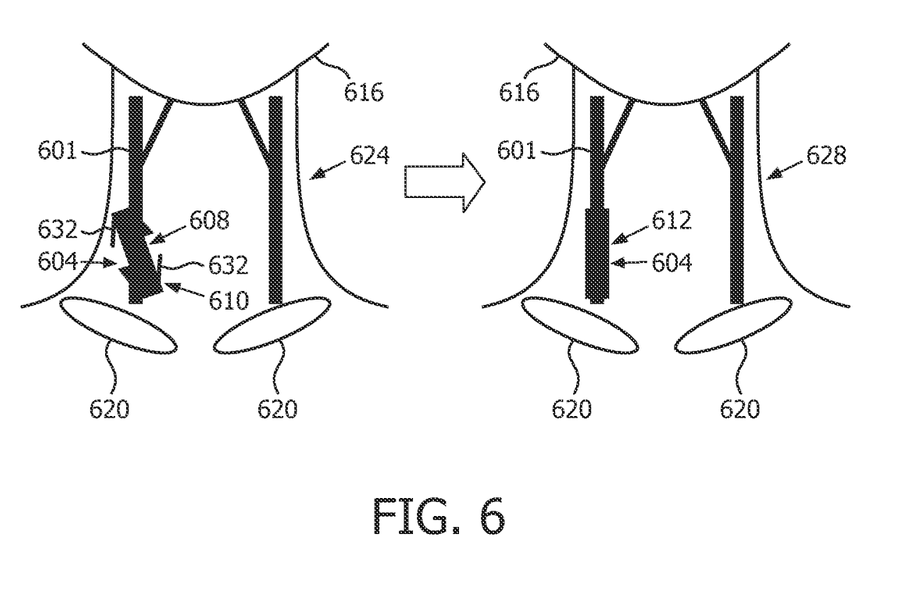
FIG. 6 is a conceptual illustration of examples of user feedback and feedback generation, in accordance with the present invention.

FIG. 6 is a specific example of user feedback and feedback generation. This example relates to the left medial common carotid artery 601 and acquiring a standard view of the artery. A transducer array face graphic 604 is shown in an oblique position 608, representative of a current placement 610 of the probe 144, and in a non-oblique position 612. The transducer array may be a linear array or a matrix array. Mandible graphics 616 and clavicle graphics 620 are also shown in FIG. 6. A current graphic 624 corresponds conceptually to the current view 502, and a target graphic 628 corresponds conceptually to the target view 510. In addition, both graphics 624, 628 may be displayed onscreen in addition to, or in place of, any other graphic or ultrasound image representative of the current view 502.

In the state space embodiment, the viewed anatomy label for a matched database image is "left medial common carotid artery, oblique view." The probe position label is "midway between clavicle and mandible." The clavicle and mandible graphics 616, 620 represent surrounding tissue. The probe orientation label is "oblique." The imaging mode label is "B-mode." An imaging setting label is "spatial compounding." An artifact label is "artifact-free." An image quality label is "good image contrast", based for example on average pixel intensity. All of the labels can be displayed, on the display 124, upon matching to the database image 604.

If an image quality attribute of the matched database image indicated lack of good probe contact, rather than the actual indication here of "good" probe contact by virtue of good image quality, this current imaging condition could interfere with further matching to database images in navigating a trajectory toward a standard view. Accordingly, improvement of the contact would predominate over other navigational considerations. This would then constitute an example of selecting an optimal trajectory in the state space, and is evidenced by the issuance of a user feedback message like "reapply gel and restore probe to the same location and orientation" that was linked to the current database image in the linking step S436.

However, since the image quality label indicates that contact is good, a different instruction, that was stored during database building in step S436, is sent for viewing on the display 124. The instruction here would be the instruction 526 to "rotate in-place clockwise." This is indicated by illustrative arrows 632. The resulting movement of the probe 144 by the clinician is, as mentioned herein above, monitored in real time via the feedback loop in steps S228 to S248. The instruction is resent for display repeatedly, but will change in the event of the current view 502 matching to a new database image, such as that corresponding to the target view 510.

In the case of the 3D image embodiment, the instruction 526 "rotate clockwise" is derivable almost by definition, since the only transformation involved in registering the current view 502 to the 3D reference image is, in fact, the clockwise rotation. In a less clearcut case, where reaching the target view 510 entails, for instance, probe in-place rotation and translation, whether rotation or translation predominates is decided by the apparatus 100. The criteria can involve thresholds selected based on empirical experience, although, for example, location will ordinarily dominate over tilting until the probe location is close to that needed for a target view 510.

Guidance in acquiring ultrasound imaging of a subject to achieve a target view, such as a standard view, entails emitting ultrasound to the subject and receiving, in response, a current ultrasound view; matching the received image to a pre-existing image, such as a three-dimensional reference image; and, for user assistance, generating, based on the matching, feedback for the guidance. The reference image may be a statistical atlas or it may be derived from patient-specific CT or MR scans. The pre-existing image may instead be a database image corresponding to a state in a state space. The feedback can be an image derived from the reference image; a graphic indication of a plane of the target view; the received view fused to an image derived from the reference image; or the received view and an image derived from said reference image, the derived image appearing concurrently and enhanced to spatially indicate where the received view registers to the reference image. The target view may be a view of a body organ, or vessel, of the subject. Both the atlas and database can be specialized for imaging of a user selected organ, or vessel, and its surrounding tissue.

In addition to making diagnostic cardiac examination performable by nurses or other clinicians who may be untrained specifically in sonography, the interactive visual guidance apparatus 100 can guide novice sonographers. Alternatively, the novel visual feedback of the apparatus 100 can speed up the work flow of trained or experienced sonographers.

While the invention has been illustrated and described in detail in the drawings and foregoing description, such illustration and description are to be considered illustrative or exemplary and not restrictive; the invention is not limited to the disclosed embodiments.

For example, the probe 144 may alternatively or additionally use tactile feedback on the appropriate probe movement toward a standard view.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus configured for guidance in acquiring ultrasound imaging of a subject to achieve a target view, said apparatus comprising:
an imaging probe for emitting ultrasound to said subject and for, in response, receiving a current ultrasound view; and
a processor and a computer-readable memory in communication with the processor, the processor being configured to:
identify, based on the received current ultrasound view, a matched image in a database of images organized as a state space comprising dimensions representative of a plurality of image attributes of the images, wherein the matched image is associated with a first image attribute of the plurality of image attributes, and wherein the database further comprises a target image corresponding to the target view;
determine, based on the first image attribute of the matched image, a trajectory within the state space between the matched image and the target image; and
generate, based on the trajectory, user feedback for guiding the ultrasound imaging of the subject to achieve the target view.

2. The apparatus of claim 1, said target view being a view of a body organ, or vessel, of a patient.

3. The apparatus of claim 1, said probe comprising a current placement, said processor configured for, by displaying via a display an outline of a body organ of the subject in relation to said received current ultrasound view and said target view, visually showing how to move said probe from its current placement so as to thereby realize the achieving of said target view.

4. The apparatus of claim 1, wherein the processor is configured for automatically in response to determining that the matched image corresponds to the target view, generating an indicator to notify the user that the target view has been achieved.

5. The apparatus of claim 1, said target view being a standard anatomical view that, prior to a time of said guidance, has already been set by a medical entity.

6. The apparatus of claim 1, wherein the processor is configured to:
receive a further current ultrasound view;
register the received further current ultrasound view to a three-dimensional reference image; and
generate, based on the registration of the further current ultrasound view, the user feedback for guiding the ultrasound imaging of the subject to achieve the target view.

7. The apparatus of claim 6, wherein the processor is configured for performing said registering, dynamically or continually.

8. The apparatus of claim 6, said reference image comprising an atlas or an image acquired of said subject via medical imaging.

9. The apparatus of claim 8, said reference image comprising said atlas, said atlas comprising a statistical atlas.

10. The apparatus of claim 6, wherein the processor is configured for concurrently visualizing, via a display, a) an image derived from said reference image; and b) a graphic indication of a plane of said target view.

11. The apparatus of claim 6, wherein the processor is configured for visualizing, via a display, one or more of: said received further current ultrasound view fused to an image derived from said reference image; and said received further current ultrasound view alongside the image derived from said reference image, the derived image appearing concurrently with the received further current ultrasound view to spatially indicate where said received further current ultrasound view registers to said reference image.

12. The apparatus of claim 6, wherein the processor is configured to generate the user feedback by generating at least one of a visual indication or audible language instructions instructing a user how to move the probe for the achieving of said target view, said apparatus further comprising at least one of a speaker for said instructing by issuing the audible language instructions, or a display for said instructing by outputting the visual indication on said display.

13. The apparatus of claim 1, wherein the target view is associated with pre-set Doppler settings, and wherein the processor is further configured for, automatically by default, initializing the apparatus with the pre-set Doppler settings.

14. The apparatus of claim 1, said processor being configured to:
determine a plurality of trajectories, including the trajectory, between the current ultrasound view and the target view, and
select the trajectory based on a prioritization of trajectories in said state space.

15. The apparatus of claim 1, wherein the processor is configured for forming said state space, said forming comprising:
receiving a plurality of images specialized for a specific body organ, or vessel, such that said organ or vessel, and/or surrounding tissue, are depicted in all of the plurality of images, the plurality of images being from multiple imaging subjects; and
labeling the plurality of images with the plurality of image attributes.

16. The apparatus of claim 15, said forming further comprising linking, to particular images from among said plurality of images, respective instructions on how to navigate said imaging probe from said particular image to another one of said plurality images.

17. The apparatus of claim 1, wherein the plurality of image attributes correspond to one or more of: a probe position, a probe orientation, an image setting, an imaging mode, a quality factor, a presence of an artifact, a particular view of an anatomical feature, and a presence of an anatomical feature.

18. The apparatus of claim 17, wherein the first image attribute corresponds to the probe position.

19. The apparatus of claim 17, wherein the matched image is also associated with a second image attribute, wherein the second image attribute corresponds to the quality factor.

20. A non-transitory computer readable medium embodying a computer program for guidance in acquiring ultrasound imaging of a subject to achieve a target view, said program comprising instructions executable by a processor for performing a plurality of acts comprising:
controlling an imaging probe to emit ultrasound energy to said subject;
in response, receiving, via the imaging probe, a current ultrasound view;
identifying, based on the received current ultrasound view, a matched image in a database comprising a plurality of images organized as a state space, the database comprising dimensions representative of a plurality of image attributes of the images, wherein the matched image is associated with a first image attribute of the plurality of image attributes, and wherein the database further comprises a target image corresponding to the target view;

determining, based on the first image attribute of the matched image, a trajectory within the state space between the matched image and the target image; and based on the trajectory, generating feedback for said guidance.

* * * * *